United States Patent
Kalb et al.

(10) Patent No.: US 11,458,658 B2
(45) Date of Patent: Oct. 4, 2022

(54) METHOD FOR MANUFACTURING AN INJECTION DEVICE WITH A BYPASS CHANNEL AND TOOL FOR THIS PURPOSE

(71) Applicant: Gerresheimer Regensburg GmbH, Regensburg (DE)

(72) Inventors: Franz Kalb, Pfreimd (DE); Christian Lanzl, Bernhardswald (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 664 days.

(21) Appl. No.: 16/377,547

(22) Filed: Apr. 8, 2019

(65) Prior Publication Data

US 2019/0315028 A1 Oct. 17, 2019

(30) Foreign Application Priority Data

Apr. 11, 2018 (DE) ...................... 10 2018 108 549.4

(51) Int. Cl.
| | |
|---|---|
| *B29C 45/14* | (2006.01) |
| *A61M 5/31* | (2006.01) |
| *B29C 51/10* | (2006.01) |
| *B29L 31/00* | (2006.01) |

(52) U.S. Cl.
CPC ........... *B29C 45/14* (2013.01); *A61M 5/3129* (2013.01); *B29C 51/10* (2013.01); *A61M 2005/3132* (2013.01); *A61M 2207/10* (2013.01); *B29C 2791/006* (2013.01); *B29L 2031/7544* (2013.01)

(58) Field of Classification Search
CPC ... B29C 45/14; B29C 51/10; B29C 2791/006; B29C 55/24; B29C 67/00; B29L 2031/7544

See application file for complete search history.

(56) References Cited

U.S. PATENT DOCUMENTS

| | | | |
|---|---|---|---|
| 3,686,051 A | 8/1972 | Samuel et al. | |
| 3,932,093 A | 1/1976 | Maier | |
| 2008/0230961 A1 | 9/2008 | Moesli et al. | |
| 2010/0096773 A1* | 4/2010 | Boucherie ........... | A61M 5/3129 264/277 |

FOREIGN PATENT DOCUMENTS

| | | |
|---|---|---|
| DE | 2925858 | 1/1981 |
| DE | 2007014281 | 9/2008 |
| DE | 102011107764 | 1/2013 |
| FR | 2244609 | 9/1973 |

\* cited by examiner

*Primary Examiner* — Jeffrey M Wollschlager
*Assistant Examiner* — Xue H Liu
(74) *Attorney, Agent, or Firm* — Simpson & Simpson, PLLC

(57) ABSTRACT

A tool and a method for manufacturing a bypass in an injection device are disclosed. The preforms of the injection device are inserted into a tool. A partial region of the cylindrical portion is heated by a heat source. The heated partial region of the cylindrical portion is plastically deformed with a male die part of the tool, so that the bypass channel is formed.

4 Claims, 1 Drawing Sheet

METHOD FOR MANUFACTURING AN INJECTION DEVICE WITH A BYPASS CHANNEL AND TOOL FOR THIS PURPOSE

CROSS-REFERENCE TO RELATED APPLICATIONS

This non-provisional patent application claims priority under 35 U.S.C. § 119 of German Patent Application No. 10 2018 108 549.4, which was filed in Germany on Apr. 11, 2018, and which is herein incorporated by reference.

FIELD OF THE INVENTION

Field of the Invention

The invention relates to a method for manufacturing an injection device with a bypass channel. Furthermore, the invention relates to a tool for the method for manufacturing an injection device with a bypass channel.

Description of the Background Art

German patent application DE 10 2007 014 281 A1 discloses a method for producing a multi-chamber syringe with a bypass channel. For this purpose, first a preform is produced of a thermoformable plastic with a tubular section. The preform is enclosed in the region in which the bypass channel is to be formed with a mold. The mold has formed a depression in the area of the bypass channel. The preform is heated to a temperature above the softening range of the plastic. The tubular section of the preform is positioned in the mold and applied with a pressure. Due to the pressure difference, the wall of the preform is pressed into the recesses of the mold, thereby plastically forming the bypass channel. The disadvantage of this method is that with the additional tool (mold) and the required application of pressure in the preform, the production costs and the cycle time for the production of a multi-chamber syringe with a bypass channel increase.

German patent application DE 29 25 858 A1 discloses a folding core with which undercuts can be formed in the interior of injection molded parts. The folding core could also be used to form the bypass channel in the injection syringe. However, the folding core is mechanically complex and would also lead to separation edges and particle formation during the injection molding process of the injection syringe.

Another possibility of forming the bypass channel in the injection syringe is to use insert components that form the bypass channel during the injection molding process. This would require a second tool, resulting in longer cycles in the manufacture of injection syringes. These longer cycles and the second tool thus increase the part prices for the injection syringe provided with the bypass channel. The handling with the insert components also leads to longer cycle times, higher costs and the particle formation cannot be excluded during the injection molding process.

The bypass channel in the injection syringe could also be manufactured by a two-component injection molding process. However, the two-component injection molding has the disadvantage that this leads to higher tool costs and a lower occupancy of the tool. The tool itself is very complex and therefore vulnerable. In the end, the two-component injection also leads to higher parts prices.

BRIEF SUMMARY OF THE INVENTION

An object of the invention is to provide a method for manufacturing an injection device with a bypass channel, which is easy and reliable to handle and reduces the cost per manufactured injection device.

This object is achieved by a method for manufacturing an injection device with a bypass channel, which comprises: inserting a preform into a tool so that the preform partially rests with a cylindrical outer surface of a cylindrical portion in the tool; heating a partial region of the cylindrical portion; inserting a male die part into the cylindrical portion substantially in an axial direction; displacing the male die part in a radial direction on a cylindrical inner surface of the cylindrical portion of the preform and pressing the male die part into the heated partial region of the cylindrical portion and thereby forming the bypass channel by plastic deformation of the heated partial region.

Furthermore, an object of the invention is to provide a tool for manufacturing an injection device with a bypass channel, with which the bypass channel can be formed in the injection device in a simple, reliable and cost-effective manner.

This object is achieved by a tool that comprises the features for manufacturing an injection device with a bypass channel, wherein the tool is configured such that it supports at least one cylindrical portion of the preform, characterized in that the tool comprises: a heat source is arranged in the tool for heating a partial region of the cylindrical portion of the preform opposite a cylindrical outer surface of the cylindrical portion; and a male die part of the tool is provided, which can be moved into the preform in an axial direction and in the preform in a radial direction towards the heated partial region.

SUMMARY OF THE INVENTION

The inventive method for manufacturing an injection device with a bypass channel is characterized in that first a preform is inserted into a tool. In this case, the preform partially rests with a cylindrical outer surface of a cylindrical portion in the tool. Subsequently, a heating of a partial region of the cylindrical portion is carried out. In parallel, a male die part (stamp) can be inserted into the cylindrical portion substantially in an axial direction. When the male die part is in the heated partial region position, the male die part is displaced in a radial direction toward a cylindrical inner surface of the cylindrical portion of the preform. The male die part is then pressed into the heated partial region of the cylindrical portion and thereby the bypass channel is formed by plastic deformation of the heated partial region.

The inventive method has the advantage that the bypass channel is formed by means of the male die part, e.g. after the injection molding process. By using the male die part cost consuming resources can be saved and in the body of the injection syringe no particles or separations accrue, which would lead to contamination of the finished product.

In an embodiment of the method of the invention, the partial region of the cylindrical portion is warmed or heated with a heat source. With the heat source, the material of the partial region is brought to a temperature such that the material of the preform can be plastically deformed by the pressure of the male die part in the radial direction. In an embodiment of the invention, the warming or heating of the partial region of the cylindrical portion is performed by means of the heat source by radiant heat and/or contact heat.

In an embodiment of the method of the invention, the preform for the injection device is injection molded from cyclo-olefin copolymer (COC), cyclic olefin polymer (COP) or polypropylene (PP).

In an embodiment of the method of the invention, by impressing the male die part in the heated partial region of the cylindrical portion a plastic deformation is carried out, by which an undercut in the partial region of the cylindrical portion is formed. The undercut defines the bypass channel which is forced outwardly from the cylindrical inner surface of the preform.

The tool for manufacturing an injection device with a bypass channel is also characterized in that it is configured such that a preform of the injection device is supported in the tool in at least one cylindrical portion. A heat source in the tool is arranged to heat a partial region of the cylindrical portion of the preform opposite a cylindrical outer surface of the cylindrical portion. Furthermore, the tool comprises a male die part, which is movable into the preform in an axial direction. Likewise, the male die part is configured such that it is movable in the preform in a radial direction towards the heated partial region.

In an embodiment of the tool of the invention, the heat source is configured as a contact heat source and/or as a radiant heat source. In a further embodiment of the tool of the invention, the tool has formed a stop for a handle of the preform for positioning of the preform in the tool. This has the advantage that the preform with the partial area to be heated is reproducibly positioned opposite to the heat source of the tool.

In an embodiment of the tool of the invention, the male die part itself is attached to a handle by means of which the male die part is insertable into the preform in the axial direction. Likewise, the preform can be moved in the radial direction toward the heated partial area via the handle. By means of the handle of the male die part, a pressure can be exerted on the heated partial region with the male die part in such a way that the male die part forms the base channel in the heated material of the cylindrical portion or of the partial region of the preform. After cooling, the injection device with the formed bypass channel can be removed from the tool.

These and other objects, features, and advantages of the present invention will become readily apparent upon a review of the following detailed description of the invention, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION OF THE INVENTION AND EMBODIMENTS

At the outset, it should be appreciated that like drawing numbers on different drawing views identify identical, or functionally similar, structural elements. It is to be understood that the claims are not limited to the disclosed aspects. The illustrated embodiment for the formation of a bypass channel for an injection device represents only one possible embodiment of how the inventive method can be configured. This is not to be construed as limiting the invention.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims.

Moreover, as used herein, "and/or" is intended to mean a grammatical conjunction used to indicate that one or more of the elements or conditions recited may be included or occur. For example, a device comprising a first element, a second element and/or a third element, is intended to be construed as any one of the following structural arrangements: a device comprising a first element; a device comprising a second element; a device comprising a third element; a device comprising a first element and a second element; a device comprising a first element and a third element; a device comprising a first element, a second element and a third element; or, a device comprising a second element and a third element.

Figure 1:
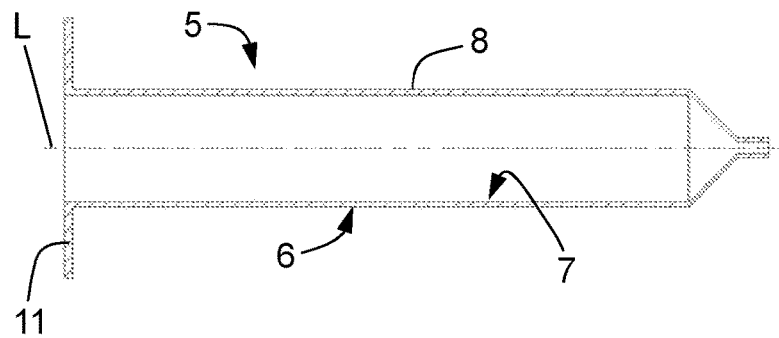
FIG. 1 is a sectional view of a preform along a longitudinal axis.
Figure 4:
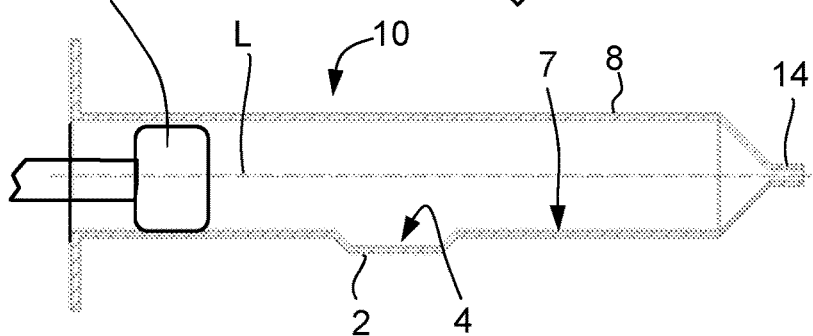
FIG. 4 is a sectional view of the injection device according to the invention with the formed bypass channel.

Adverting now to the Figures, FIG. 1 shows a sectional view of a preform 5 for the manufacture of an injection device 10 with a bypass channel 2 (see FIG. 4). The preform 5 consists of a cylindrical portion 8, which is aligned along a longitudinal axis L. The cylindrical portion 8 defines a cylindrical outer surface 6 and a cylindrical inner surface 7. Similarly, the preform 5 has formed a handle 11, which can be used in the manufacturing process for the positioning of the preform 5 in a tool 20 (see FIG. 2).

Figure 2:
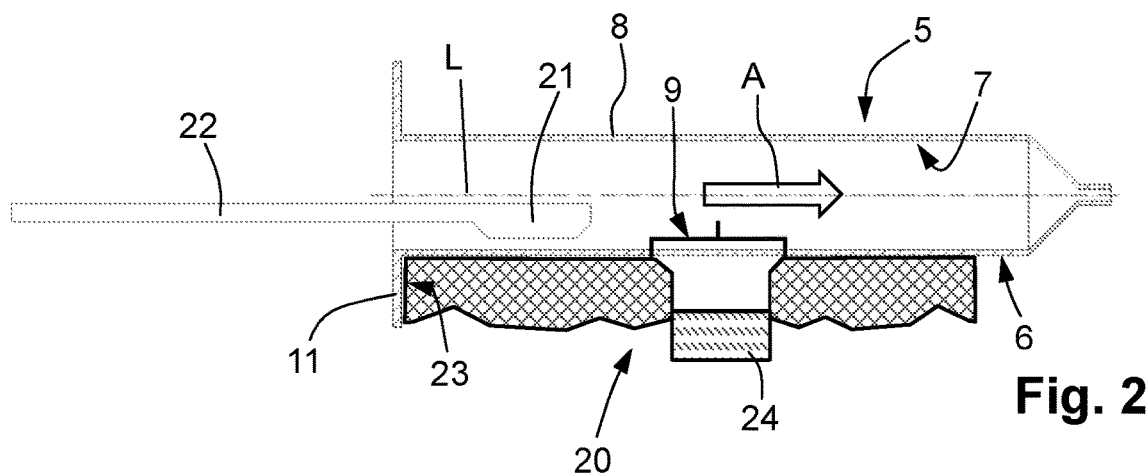
FIG. 2 is a sectional view of the preform shown in FIG. 1 positioned in the tool.

FIG. 2 likewise shows a sectional view along the longitudinal axis L of the preform 5. The preform 5 is already positioned in a specially configured tool 20 here. The tool defines a stop 23, which cooperates with the handle 11 of the preform 5. As a result, a reproducible positioning of the preform 5 in the tool 20 is achieved. The tool 20 also includes a heat source 24 suitable for heating a partial region 9 of the cylindrical portion 8 of the preform 5. The heat source 24 may be in the form of a contact heat source and/or a radiant heat source. The preform 5 thus rests with a cylindrical outer surface 6 of the cylindrical portion 8 in the tool. The heat source 24 heats the partial region 9 of the cylindrical portion 8 to a temperature such that the material of the preform 5 can be plastically deformed. Simultaneously with the heating of the partial region 9 of the cylindrical portion 8, a male die part 21 can be inserted in the axial direction A in the preform 5. Preferably, the male die part 21 is attached to a handle 22.

Figure 3:
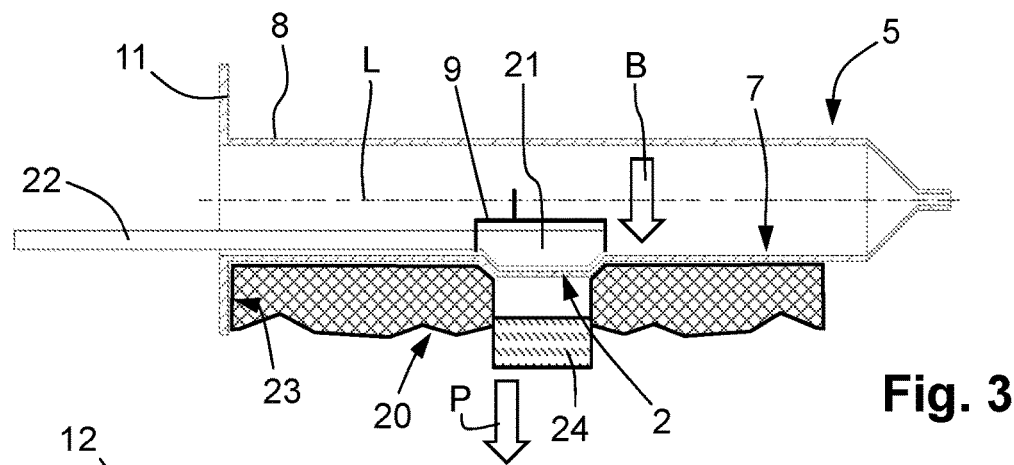
FIG. 3 is a sectional view of the preform positioned in the tool and in which the bypass channel is formed.

FIG. 3 shows the situation that the male die part 21 has been moved in a radial direction B toward the partial region 9 of the cylindrical portion 8. Preferably, the preform 5 is injection molded from a thermoplastic material. In particular, for the preform 5, the materials COC, COP and PP are used. The movement of the male die part 21 in the radial direction B is effected substantially by the handle 22. As soon as the male die part 21 reaches the cylindrical inner surface 7 of the cylindrical portion 8, a pressure P in the radial direction B is exerted on the male die part 21 via the handle 22, which ensures plastic deformation of the heated partial region 9.

FIG. 4 shows a sectional view of the injection device 10 produced by the method according to the invention along the longitudinal axis L. The bypass channel 2 is formed in the cylindrical portion 8. In this case, the cylindrical portion 8 is arched outwards from the cylindrical inner surface 7 in the partial region 9 (see FIGS. 2 and 3), so that thereby the cylindrical portion 8 of the injection device 10 has formed an undercut 4. Furthermore, a piston 12 can be inserted into the injection device 10, with which the material present in the injection device 10 can be discharged through a nozzle 14 of the injection device 10.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

LIST OF REFERENCE SIGNS

2 Bypass channel
4 Undercut
5 Preform
6 Cylindrical outer surface
7 Cylindrical inner surface
8 Cylindrical portion
9 Partial region
10 Injection device
11 Handle
12 Piston
14 Nozzle
20 Tool
21 Male die part
22 Handle
23 Stop
24 Heat source
A Axial direction
B Radial direction
L Longitudinal axis
P Pressure

What is claimed is:

1. A tool for manufacturing an injection device with a bypass channel, wherein the tool is configured such that it supports at least one cylindrical portion of a preform, the tool comprises:
   a heat source arranged in the tool that heats a partial region of the cylindrical portion of the preform opposite a cylindrical outer surface of the cylindrical portion; and
   a male die part that is moveable into the preform in an axial direction and in the preform in a radial direction towards the heated partial region, the heated partial region corresponding to the bypass channel that is to be formed in the injection device.

2. The tool according to claim 1, wherein the heat source is a contact and/or radiant heat source.

3. The tool according to claim 1, wherein the tool has formed a stop for a handle of the preform, so that the preform with the partial region to be heated is reproducibly positioned opposite to the heat source of the tool.

4. The tool according to claim 1, wherein the male die part is attached to a handle, by means of which the male die part is insertable into the preform in the axial direction, movable in the preform in the radial direction towards the heated partial region, and a pressure is exercisable on the heated partial region, so that the male die part forms the bypass channel.

* * * * *